United States Patent
Bauer

(10) Patent No.: US 7,183,932 B2
(45) Date of Patent: Feb. 27, 2007

(54) INTER-VEHICLE DROWSY DRIVER ADVISORY SYSTEM

(75) Inventor: James Anthony Bauer, Ypsilanti, MI (US)

(73) Assignee: Toyota Technical Center USA, Inc, Ann Arbor, MI (US)

(*) Notice: Subject to any disclaimer, the term of this patent is extended or adjusted under 35 U.S.C. 154(b) by 179 days.

(21) Appl. No.: 11/085,783

(22) Filed: Mar. 21, 2005

(65) Prior Publication Data

US 2006/0220915 A1  Oct. 5, 2006

(51) Int. Cl.
G08B 23/00  (2006.01)

(52) U.S. Cl. .................. 340/575; 340/576; 340/901; 340/902

(58) Field of Classification Search ............. 340/575, 340/576, 901, 902
See application file for complete search history.

(56) References Cited

FOREIGN PATENT DOCUMENTS

JP  2003123198  4/2003
JP  2004078562  3/2004

Primary Examiner—Jeffery Hofsass
Assistant Examiner—Hongmin Fan
(74) Attorney, Agent, or Firm—Gifford, Krass, Groh, Sprinkle, Anderson & Citkowski, P.C.

(57) ABSTRACT

A driver advisory system is provided for use in a host vehicle and for transmitting to drivers of other vehicles information regarding the status of a driver of the host vehicle. The driver advisory system includes a sensor, a first processor and a communication unit. The sensor monitors a physical condition of the driver of the host vehicle. The sensor provides an output quantifying the physical condition of the driver of the host vehicle. The first processor receives the output provided by the sensor. The first processor calculates a risk factor as a function of the output provided by the sensor. The first processor provides an output signal having information concerning the condition of the driver of the host vehicle in response to the risk factor exceeding a predetermined threshold value. The communication unit receives the output signal from the first processor and transmitting the information for retrieval by the other vehicles in the vicinity of the host vehicle.

23 Claims, 2 Drawing Sheets

INTER-VEHICLE DROWSY DRIVER ADVISORY SYSTEM

BACKGROUND OF THE INVENTION

1. Field of the Invention

The invention relates to a driver advisory system for use in a host vehicle for sensing a drowsy or fatigued condition of a driver of the host vehicle. More specifically, the invention system relates to a driver advisory system that provides an alert to other drivers in the vicinity of the host vehicle regarding the drowsy or fatigued condition of the driver of the host vehicle.

2. Description of the Related Art

The National Highway Traffic Safety Administration estimates that approximately 100,000 crashes annually are caused primarily by driver drowsiness or fatigue. Of these crashes, data from the Fatality Analysis Reporting System indicate that drowsiness/fatigue was a factor in crashes in which more than 1400 fatalities occurred in 1998.

Advisory systems are known for sensing the drowsy condition of the driver and providing an alert to keep the driver awake. But, these systems do not provide an alert to drivers of other vehicles as to the drowsy condition of the driver.

In Japanese Patent laid-open Application No. 2004-78562, a communication system is disclosed for transmitting information regarding the driver's status to a remote vehicle. This patent, however, does not disclose communicating information concerning the drowsiness of the driver. It also does not disclose a system for providing a warning to other vehicles regarding the drowsy condition of the driver. Further, it does not disclose a system for providing information regarding the position and location of the car with the drowsy driver.

It remains desirable to provide a driver advisory system that provides to other drivers in the vicinity of a vehicle: an alert regarding the drowsy or fatigued condition of the driver of the vehicle; and the instant location of the vehicle.

SUMMARY OF THE INVENTION

According to one aspect of the invention, a driver advisory system is provided for use in a host vehicle and for transmitting to drivers of other vehicles information regarding the status of a driver of the host vehicle. The driver advisory system includes a sensor, a first processor and a communication unit. The sensor monitors a physical condition of the driver of the host vehicle. The sensor provides an output quantifying the physical condition of the driver of the host vehicle. The first processor receives the output provided by the sensor. The first processor calculates a risk factor as a function of the output provided by the sensor. The first processor provides an output signal having information concerning the condition of the driver of the host vehicle in response to the risk factor exceeding a predetermined threshold value. The communication unit receives the output signal from the first processor and transmitting the information for retrieval by the other vehicles in the vicinity of the host vehicle.

BRIEF DESCRIPTION OF THE DRAWINGS

Advantages of the present invention will be readily appreciated as the same becomes better understood by reference to the following detailed description when considered in connection with the accompanying drawings, wherein.

DETAILED DESCRIPTION OF THE INVENTION

An embodiment of the invention provides a driver advisory system for use in a host vehicle. The advisory system detects a drowsy or fatigued condition of a driver of the host vehicle. The advisory system then broadcasts or transmits to vehicles in the vicinity of the host vehicle a message relating to the drowsy or fatigued condition of the driver. Optionally, the advisory system provides a description, position and heading of the host vehicle.

Figure 1:
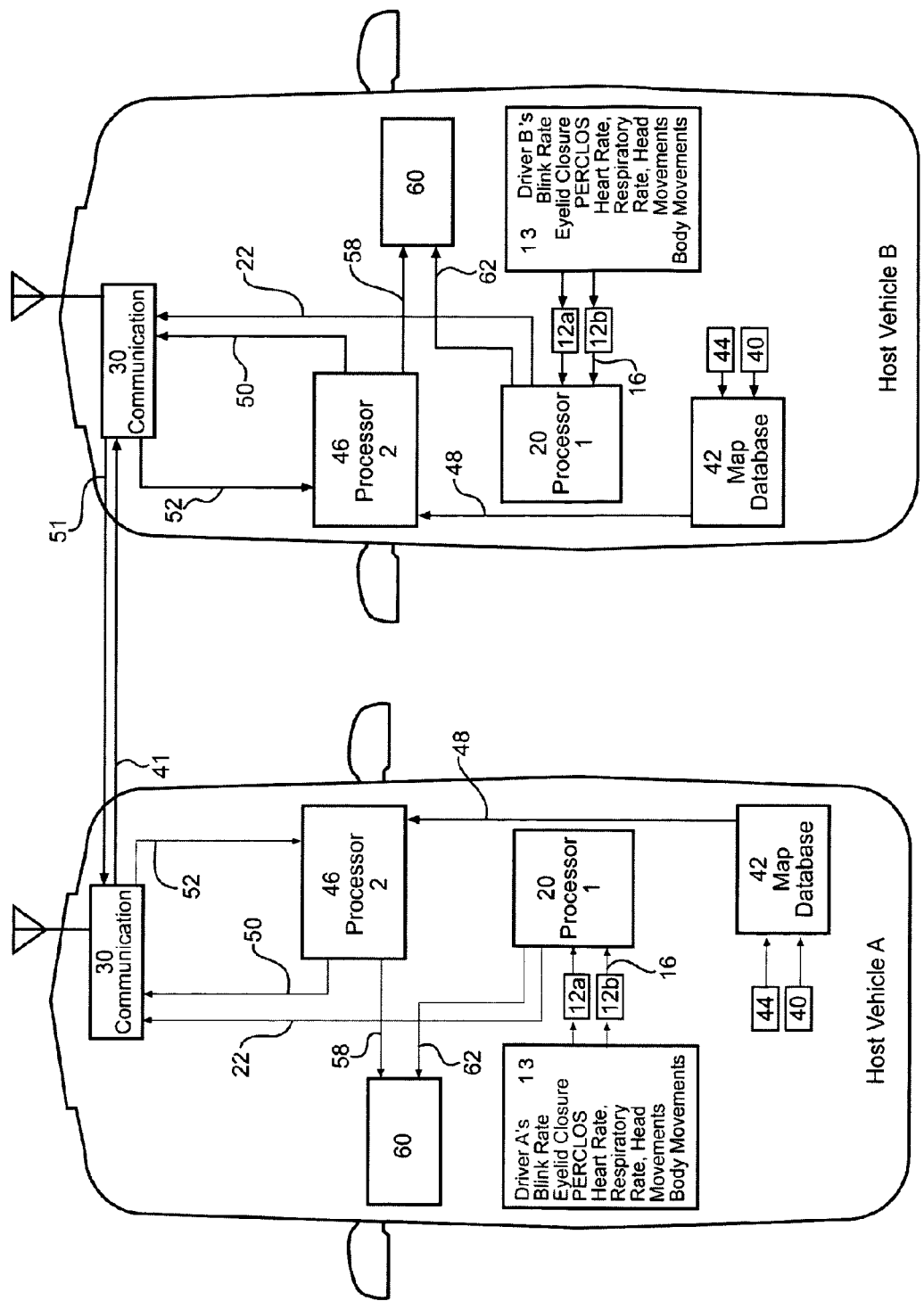
FIG. 1 is a schematic of an advisory system according to one embodiment of the invention.

The advisory system is generally indicated at 10 in FIG. 1. The advisory system 10 includes at least one sensor 12 for sensing a physical condition, such as a vital sign, reflex or body movement. Most preferably, a plurality of sensors 12 are utilized for sensing or measuring a variety of physical conditions 13 associated with driver drowsiness or fatigue, such as eyelid closure, eyelid blank rate, percent eyelid closure (PERCLOS), heart rate, respiratory rate, head movement, and body movement. The sensors 12 can be any type of suitable sensor known by those of ordinary skill in the art, such as vision based sensors 12a, and radar-based and capacitive sensors 12b. Each sensor 12 provides an output 16 quantifying the measured condition.

A first processor 20 receives the output provided by each sensor 12. The first processor 12 calculates a risk factor as a function of the outputs 16 provided by the sensors 12. The first processor 20 provides an output signal 22, in response to the risk factor exceeding a predetermined threshold value. The output signal 22 includes information concerning the drowsy or fatigue condition of the driver.

A communication unit 30 receives the output signal 22 from the first processor 20. The communication unit 30 transmits the information 41 for retrieval by other vehicles in the vicinity of the host vehicle. Preferably, the communication unit 30 is a dedicated short range communication device having a receiver and transmitter, as known by those of ordinary skill in the art. The receiver and transmitter can, for example, communicate via a radio frequency, low or high band frequencies, Bluetooth or citizen band radio.

The advisory system 10 also includes a vehicle positioning system. The positioning system includes a database 42, a global positioning system (GPS) 44 and a second processor 46. The database 42 contains a digital map of a geographical area traveled by the host vehicle. The GPS 44 provides a signal 48 corresponding to a position and a heading of the host vehicle on the digital map. The second processor 46 receives the signal 48 from the GPS 44 and provides a second output signal 50 having information relating to the position and heading of the host vehicle. Preferably, the GPS 44 receives a differential GPS correction signal 40 to offset error in the position of the host vehicle caused by the GPS 44.

The communication unit 30 receives the second output signal 50 from the second processor 46. The communication unit 30 transmits the information relating to the position and heading of the host vehicle for retrieval by the other vehicles in the vicinity of the host vehicle.

The advisory system 10 can also receive messages 51 transmitted from a second host vehicle in the vicinity of the host vehicle. Specifically, the communication unit 30 can receive messages transmitted from the second host vehicle regarding the condition of a driver of the second host vehicle, and the position and heading of the second host vehicle. The communication unit 30 then provides a signal 52 to the second processor 46 containing the information transmitted from the second host vehicle. With the signal 48 from the GPS 44 and the signal 52 from the communication unit 30, the second processor 46 calculates a distance between the host vehicle and the second host vehicle. Preferably, the distance is calculated instantaneously and continuously, while information regarding the host and second host vehicles is made readily and continuously by the GPS 44 and the communication unit 30, respectively.

The second processor 46 provides a third output signal 58 relating to the distance between the host vehicle and the second host vehicle. The second processor 46 also provides an alert signal in response to the distance between the host vehicle and the second host vehicle falling below a predetermined threshold. A human machine interface 60 receives the third output signal 58 and provides information to the driver of the host vehicle relating to the distance between the host vehicle and the second host vehicle. The human machine interface 60 also receives the alert signal and provides a warning to the driver of the host vehicle regarding the proximity of the second host vehicle.

The first processor 20 also provides a fourth output signal 62 to the human machine interface 60 concerning the condition of the driver of the host vehicle and provides an alert to the driver of the host vehicle regarding the driver's own condition. Preferably, the alert will be in the form of a stimulus for disrupting a tendency of the drowsy driver to fall asleep, such as loud audible sounds, flashing lights and the like.

Figure 2:
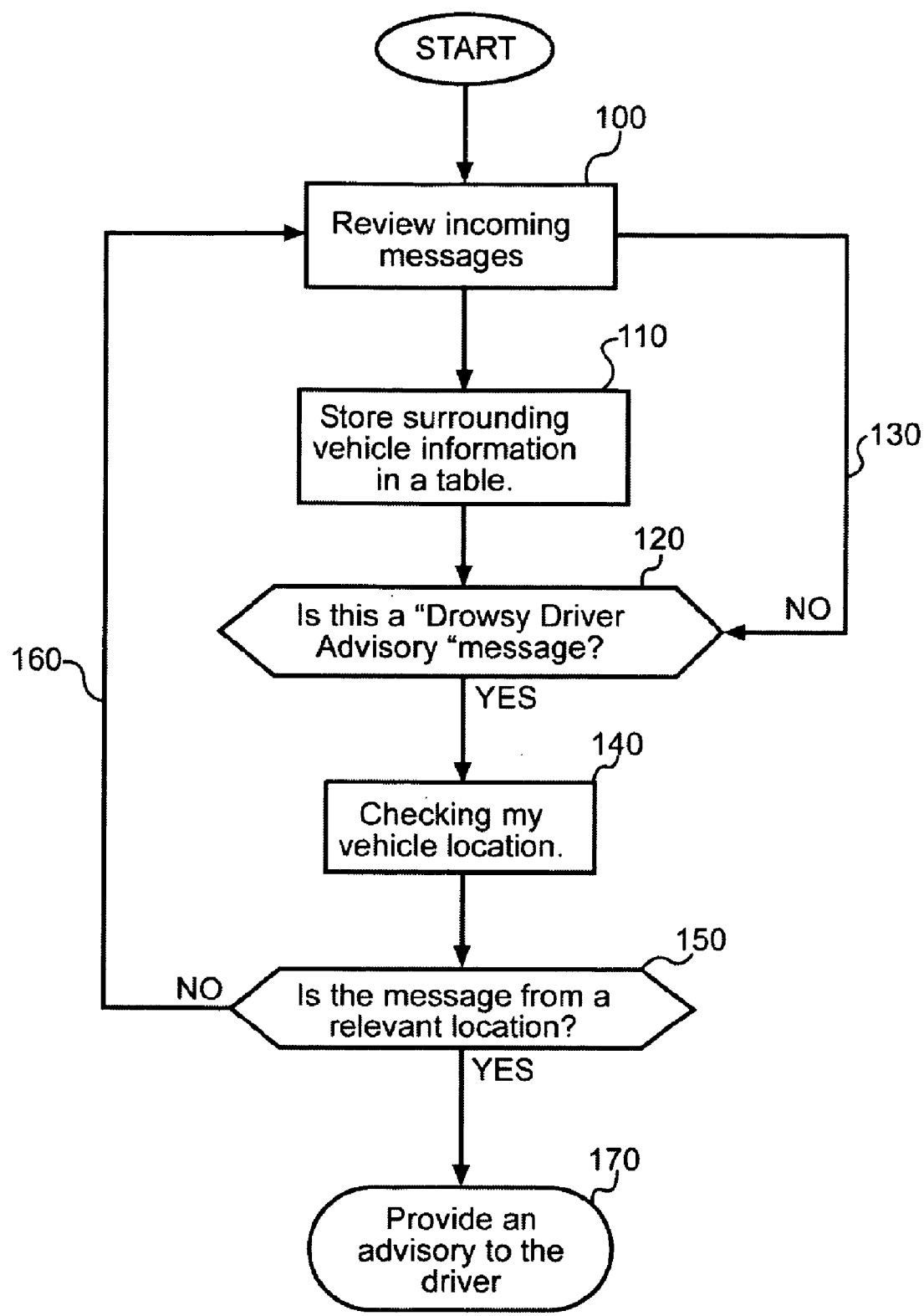
FIG. 2 is a flow chart describing a mode of operation of the advisory system of FIG. 1.

In FIG. 2, a flow chart is provided for describing one mode of operation of the advisory system 10 in the host vehicle, wherein the advisory system 10 continuously monitors for potential drowsy drivers in the vicinity of the host vehicle. The system 10 reviews 100 all incoming messages from the same or similar advisory systems in the vicinity of the vehicle. Information relating to at least a second host vehicle in the vicinity of the host vehicle is stowed 110 in a table. The system 10 then determines 120 if any of the incoming messages is a drowsy driver advisory alert provided by the second host vehicle. If the message is not a drowsy driver advisory alert, then the system continues 130 to monitor incoming messages. If the message is a drowsy driver advisory alert, then the system checks 140 the current location of the host vehicle and determines the distance between the host vehicle and the second host vehicle. The system then determines 150 if the distance falls below a predetermined threshold distance. If the distance remains above the threshold, then the system continues 160 to monitor the incoming messages. If the distance falls below the threshold distance, then the system provide 170 an advisory alert to the driver of the host vehicle relating to the drowsy condition of the driver of the second host vehicle; the instant position of the second host vehicle with respect to the host vehicle; and the instant direction or heading of the host vehicle. The system 10 continuously monitors the condition of the driver of the second host vehicle and the position and heading of the second host vehicle until incoming messages are no longer received by the system; the system in the second host vehicle determines that the driver is no longer drowsy and ceases further transmission to the host vehicle; or the distance between the host vehicle and second host vehicle lengthens beyond the threshold distance.

The invention has been described in an illustrative manner. It is, therefore, to be understood that the terminology used is intended to be in the nature of words of description rather than of limitation. Many modifications and variations of the invention are possible in light of the above teachings. Thus, within the scope of the appended claims, the invention may be practiced other than as specifically described.

I claim:

1. A driver advisory system for use in a host vehicle and for transmitting to drivers of other vehicles information regarding the status of a driver of the host vehicle, said driver advisory system comprising:
    a sensor monitoring a physical condition of the driver of the host vehicle, said sensor providing an output quantifying said physical condition of the driver of the host vehicle;
    a first processor receiving said output provided by said sensor, said first processor calculating a risk factor as a function of said output provided by said sensor, said first processor providing an output signal having information concerning a condition of the driver of the host vehicle in response to said risk factor exceeding a predetermined threshold value; and
    a communication unit receiving said output signal from said first processor and transmitting said information for retrieval by the other vehicles in the vicinity of the host vehicle.

2. A driver advisory system as set forth in claim 1 including a plurality of sensors for sensing a plurality of physical conditions of the host driver.

3. A driver advisory system as set forth in claim 2 wherein said plurality of physical conditions is selected from the group consisting of: eyelid closure, eyelid blank rate, percent eyelid closure, heart rate, respiratory rate, head movement, and body movement.

4. A driver advisory system as set forth in claim 2 wherein said plurality of sensors is selected from the group consisting of: vision based sensors, radar sensors, and capacitive sensors.

5. A driver advisory system as set forth in claim 1 including a vehicle positioning system calculating instant location of the host vehicle.

6. A driver advisory system as set forth in claim 5, wherein said vehicle positioning system comprises:
    a database containing a digital map of a geographical area traveled by the host vehicle;
    a global positioning system providing a signal corresponding to a position and a heading of the host vehicle on said digital map; and
    a second processor receiving said signal from said global positioning system, said second processor providing a second output signal having information concerning said position and heading of the host vehicle.

7. A driver advisory system as set forth in claim 6, wherein said communication unit receives said second output signal from said second procssor and transmits said information concerning said position and heading of the host vehicle for retrieval by the other vehicles in the vicinity of the host vehicle.

8. A driver advisory system as set forth in claim 6, wherein said vehicle positioning system receives a differential global positioning system correction signal to offset error in said position of the host vehicle caused by the global positioning system.

9. A driver advisory system as set forth in claim 6, wherein said communication unit receives messages transmitted from a second host vehicle regarding the condition of a driver of the second host vehicle, and a position and heading of the second host vehicle.

10. A driver advisory system as set forth in claim 9, wherein said second processor receives a signal from said communication unit concerning the position and heading of the second host vehicle, allowing said second processor to calculate and provide a third output signal relating to a distance between the host vehicle and the second host vehicle.

11. A driver advisory system as set forth in claim 10, wherein said second processor provides an alert signal in response to said distance between the host vehicle and the second host vehicle falling below a predetermined threshold.

12. A driver advisory system as set forth in claim 10 including a human-machine interface receiving said third output signal from said second processor and providing information to the driver of the host vehicle regarding said distance between the host vehicle and the second host vehicle.

13. A driver advisory system as set forth in claim 11, wherein said human machine interface receives said alert signal from said second processor and provides a warning to the driver of the host vehicle regarding the proximity of the second host vehicle.

14. A driver advisory system as set forth in claim 12, wherein said first processor provides a fourth output signal to said human machine interface concerning the condition of the driver of the host vehicle and provides an alert to the driver of the host vehicle regarding the driver's own condition.

15. A driver advisory system as set forth in claim 1, wherein said output signal from said first processor includes information regarding make and model of the host vehicle.

16. A method of transmitting to drivers of other vehicles information regarding the status of a driver of a host vehicle, the method comprising the steps of:
  monitoring a physical condition of the driver of the host vehicle;
  providing an output quantifying the physical condition of the driver of the host vehicle;
  calculating a risk factor as a function of the output;
  transmitting the information concerning the condition of the driver of the host vehicle for retrieval by the other vehicles in the vicinity of the host vehicle, when the risk factor exceeding a predetermined threshold value.

17. A method as set forth in claim 16 including the step of monitoring a plurality of physical conditions of the host driver, including eyelid closure, eyelid blank rate, percent eyelid closure, heart rate, respiratory rate, head movement, and body movement.

18. A method as set forth in claim 16 including the step of calculating the instant location of the host vehicle.

19. A method as set forth in claim 18 including the step of transmitting the information concerning the instant location of the host vehicle for retrieval by the other vehicles in the vicinity of the host vehicle, in response to the risk factor exceeding a predetermined threshold value.

20. A method as set forth in claim 18 including the step of receiving messages transmitted from a second host vehicle regarding the condition of a driver of the second host vehicle, and a position and heading of the second host vehicle.

21. A method as set forth in claim 18 including the step of calculating a distance between the host vehicle and the second host vehicle.

22. A method as set forth in claim 21 including the step of providing to the driver of the host vehicle an alert signal in response to the distance between the host vehicle and the second host vehicle falling below a predetermined threshold.

23. A method of transmitting and processing information regarding the status of a driver between a first host vehicle and a second host vehicle, the method comprising the steps of:
  determining the instant location of the first host vehicle;
  receiving messages transmitted from a second host vehicle regarding the condition of a driver of the second host vehicle, and a position and heading of the second host vehicle; calculating a risk factor based on an output quantifying the physical condition of the driver of the second host vehicle;
  calculating a distance between the host vehicle and the second host vehicle; and
  providing to the driver of the first host vehicle an alert signal in response to the risk factor and the distance between the first host vehicle and the second host vehicle falling below predetermined threshold values.

* * * * *

UNITED STATES PATENT AND TRADEMARK OFFICE
CERTIFICATE OF CORRECTION

PATENT NO. : 7,183,932 B2
APPLICATION NO. : 11/085783
DATED : February 27, 2007
INVENTOR(S) : James A. Bauer It is certified that error appears in the above-identified patent and that said Letters Patent is hereby corrected as shown below:

Column 6, line 33, move "calculating a risk factor based on" to line 34.

Signed and Sealed this

Twelfth Day of June, 2007

JON W. DUDAS
*Director of the United States Patent and Trademark Office*